United States Patent
Gueremy et al.

[11] Patent Number: 5,340,824
[45] Date of Patent: * Aug. 23, 1994

[54] BENZOTHIAZOLE DERIVATIVES AND MEDICINAL PRODUCTS CONTAINING THEM

[75] Inventors: Claude Gueremy, Houilles; Patrick Jimonet, Villepreux; Serge Mignani, Paris, all of France

[73] Assignee: Rhone-Poulenc Rorer S.A., Antony Cedex, France

[*] Notice: The portion of the term of this patent subsequent to Dec. 25, 2007 has been disclaimed.

[21] Appl. No.: 938,153

[22] PCT Filed: May 31, 1991

[86] PCT No.: PCT/FR91/00437
§ 371 Date: Dec. 2, 1992
§ 102(e) Date: Dec. 2, 1992

[87] PCT Pub. No.: WO91/18892
PCT Pub. Date: Dec. 12, 1991

[30] Foreign Application Priority Data
Jun. 7, 1990 [FR] France .................. 90 07068

[51] Int. Cl.⁵ .................. A61K 31/44; C07D 417/12
[52] U.S. Cl. .................. 514/321; 514/367; 546/198; 548/164
[58] Field of Search .................. 548/164; 546/198; 514/321, 367

[56] References Cited
U.S. PATENT DOCUMENTS

| | | | |
|---|---|---|---|
| 4,370,338 | 1/1983 | Mizoule | 548/152 |
| 4,980,356 | 12/1990 | Audiau et al. | 548/161 |
| 5,008,280 | 4/1991 | Gueremy et al. | 514/367 |
| 5,026,717 | 6/1991 | Audiau et al. | 514/338 |

FOREIGN PATENT DOCUMENTS
356234 2/1990 European Pat. Off. .

*Primary Examiner*—Joseph Paul Brust
*Assistant Examiner*—Mary Susan H. Gabilan
*Attorney, Agent, or Firm*—Morgan & Finnegan

[57] ABSTRACT

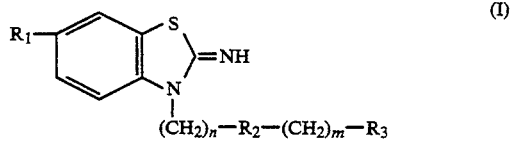

Compounds of formula (I), in which $R_1$ is a polyfluoralkoxy, $R_2$ is a sulphur or nitrogen atom substituted by an alkyl radical or a sulfonyl or sulfinyl radical, $R_3$ is a phenyl, benzoyl, —$NR_4R_5$ or piperidinyl-4radical substituted in position 1 by a phenylalkyl radical, $R_4$ is an alkyl radical, $R_5$ is a phenylalkyl radical, n is equal to 1, 2 or 3, m is equal to 0, 1, 2 or 3. The present invention also relates to the salts of said compounds, processes for the preparation of the latter and drugs containing them.

4 Claims, No Drawings

BENZOTHIAZOLE DERIVATIVES AND MEDICINAL PRODUCTS CONTAINING THEM

FIELD OF THE INVENTION

The present invention relates to compounds of formula:

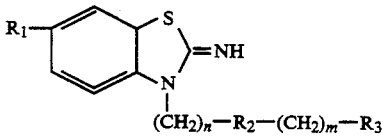
(I)

their salts, processes for preparing them and medicinal products containing them.

In the formula (I), $R_1$ represents a polyfluoroalkoxy radical, $R_2$ represents a sulphur or nitrogen atom which is substituted by an alkyl radical or a sulphonyl or sulphinyl radical, $R_3$ represents a phenyl radical, a benzoyl radical, an $NR_4R_5$ radical or a 4-piperidyl radical which is substituted in position 1 by a phenylalkyl radical, $R_4$ represents an alkyl radical, $R_5$ represents a phenylalkyl radical, n is equal to 1, 2 or 3, m is equal to 0, 1, 2 or 3.

In the above definitions and in those which will be mentioned below, the alkyl and alkoxy radicals and the alkyl and alkoxy moieties contain 1 to 4 carbon atoms in a linear or branched chain.

The polyfluoroalkoxy radicals are preferably trifluoromethoxy, pentafluoroethoxy, 2,2,2-trifluoroethoxy or 1,1,2,2-tetrafluoroethoxy radicals.

The invention also relates to the addition salts of the compounds of formula (I) with inorganic or organic acids.

DETAILED DESCRIPTION OF THE INVENTION

The compounds of formula (I) for which $R_2$ represents a sulphur atom may prepared by hydrolyzing a derivative of formula:

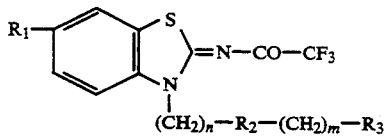
(II)

in which $R_1$, $R_3$, n and m have the same meanings as in formula (I) and $R_2$ represents a sulphur atom.

This hydrolysis is generally carried out by means of a base such as an alkali metal carbonate (preferably sodium or potassium carbonate) or concentrated ammonium hydroxide, in a water-alcohol mixture, at a temperature of between 20° C. and the boiling point of the solvent.

The derivatives of formula (II) may be obtained by the action of a sulphide of formula:

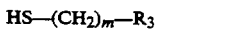
(III)

in which m and $R_3$ have the same meanings as in formula (I), on a derivative of formula:

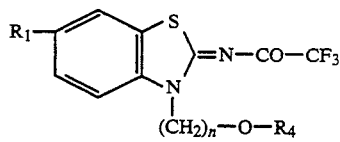
(IV)

in which $R_1$ and n have the same meanings as in formula (I) and $R_4$ represents a reactive group such as a methanesulphonyl or p-toluenesulphonyl radical.

This reaction is carried out by means of a base such as an alkali metal hydride (preferably sodium hydride), in an inert solvent such as dimethylformamide, at a temperature in the region of 25° C.

The derivatives of formula (III) for which $R_3$ represents a 4-piperidyl radical which is substituted in position 1 by a phenylalkyl radical may be prepared by applying or adapting the method described in the examples.

The derivatives of formula (IV) may be prepared by the action of a derivative of formula:

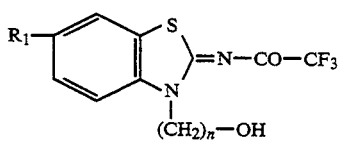
(V)

in which $R_1$ and n have the same meanings as in formula (I), on methanesulphonic or p-toluenesulphonic acid chloride, either in an inert solvent such as an aromatic solvent (for example benzene, toluene or xylene) or in a chlorine-containing solvent (for example chloroform or methylene chloride), in the presence of a tertiary amine such as triethylamine, at a temperature in the region of 20° C., or in pyridine, at a temperature in the region of 0° C.

The derivatives of formula (V) may be obtained by the action of ethyl trifluoroacetate on a derivative of formula:

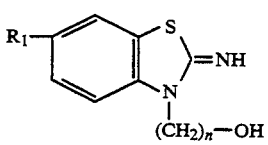
(VI)

in which $R_1$ and n have the same meanings as in formula (I).

This reaction is generally carried out in an alcohol (for example methanol or ethanol), in the presence of a tertiary amine such as triethylamine, at a temperature in the region of 20° C.

The derivatives of formula (VI) may be prepared by the action of a halogenated derivative of formula:

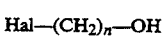
(VII)

in which n has the same meanings as in formula (I) and Hal represents a halogen atom (preferably bromine or chlorine), on a 2-amino-6-polyfluoroalkoxybenzothiazole.

This reaction is carried out in an alcohol (preferably ethanol or methanol) at the boiling point of the solvent.

The 2-amino-6-polyfluoroalkoxybenzothiazoles may be prepared by applying or adapting the method described by L.M. YAGUPOL'SKII et al., Zh. Obshcho Khim., 33(7), 2301 (1963).

The compounds of formula (I) for which $R_2$ represents a sulphur atom may also be obtained by the action of a 2-amino-6-polyfluoroalkoxybenzothiazole on a derivative of formula:

$$Hal-(CH_2)_n-R_2-(CH_2)_m-R_3 \qquad (VIII)$$

in which n, m and Ra have the same meanings as in formula (I), $R_2$ represents a sulphur atom and Hal represents a halogen atom (preferably chlorine and bromine).

This reaction is generally carried out in an inert solvent such as an alcohol (for example methanol or ethanol) or a ketone (for example methyl ethyl ketone), at a temperature of between 20° C. and the boiling point of the solvent.

The derivatives of formula (VIII) may be obtained by applying or adapting the method described by KULKA et al., Can. J. Chem., 35, 519 (1957), or by halogenating a derivative of formula:

$$HO-(CH_2)_n-R_2-(CH_2)_m-R_3 \qquad (IX)$$

in which n, m and $R_3$ have the same meanings as in formula (I) and $R_2$ represents a sulphur atom.

This reaction is carried out by means of a halogenating agent (for example thionyl chloride or thionyl bromide), in an ether (for example diethyl ether), at the boiling point of the solvent.

The derivatives of formula (IX) may be obtained by the action of a derivative of formula:

$$HO-(CH_2)_n-SH \qquad (X)$$

in which n has the same meanings as in formula (I), on a derivative of formula:

$$Hal-(CH_2)_m-R_3 \qquad (XI)$$

in which m and $R_3$ have the same meanings as in the formula (I) and Hal represents a halogen atom (preferably chlorine or bromine).

This reaction is carried out by means of a base such as an alkali metal alcoholate (for example sodium or potassium ethoxide or sodium or potassium methoxide), in an inert solvent such as an alcohol, at the boiling point of the solvent.

The compounds of formula (I) for which $R_2$ represents a sulphonyl or sulphinyl radical may be obtained by oxidation of the corresponding derivatives of formula (I) for which $R_2$ represents a sulphur atom.

This oxidation is generally carried out by means of m-chloroperbenzoic acid in an inert solvent such as an alcohol (for example methanol or ethanol) or a chlorine-containing solvent (for example methylene chloride or chloroform), at a temperature of between −20° C. and 30° C.

The compounds of formula (I) for which $R_2$ represents a nitrogen atom which is substituted by an alkyl radical may be prepared by the action of bromine and an alkali metal thiocyanate on a derivative of formula:

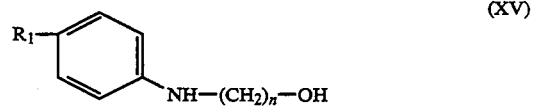

$$NH(CH_2)_n-R_2-(CH_2)_m-R_3$$

in which $R_1$, $R_3$, n and m have the same meanings as in formula (I) and $R_2$ represents a nitrogen atom which is substituted by an alkyl radical.

This reaction is preferably carried out in acetic acid, at a temperature in the region of 20° C.

Potassium thiocyanate is preferably used as the alkali metal thiocyanate.

The derivatives of formula (XII) may be obtained by the action of an amine of formula:

$$HN(R_5)-(CH_2)_m-R_3 \qquad (XIII)$$

in which $R_5$ represents an alkyl radical and $R_3$ and m have the see meanings as in formula (I), on a derivative of formula:

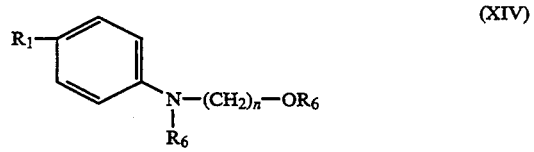

$$N-(CH_2)_n-OR_6$$
$$|$$
$$R_6$$

in which $R_1$ and n have the same meanings as in formula (I) and $R_6$ represents a p-toluenesulphonyl radical.

This reaction is generally carried out in the presence of sodium hydrogen carbonate, in an inert solvent such as dimethylformamide, at a temperature of between 50° C. and 100° C.

The derivatives of formula (XIV) may be obtained by the action of p-toluenesulphonyl chloride on a derivative of formula:

(XV)

$$R_1 \text{—} \bigcirc \text{—} NH-(CH_2)_n-OH$$

in which $R_1$ and n have the same meanings as in formula (I).

This reaction is generally carried out in an inert solvent such as a chlorine-containing solvent (for example chloroform or methylene chloride) in the presence of a tertiary amine such as triethylamine, at a temperature of between 0° C. and 30° C.

The derivatives of formula (XV) may be obtained by the action of a 4-polyfluoroalkoxyaniline on a derivative of formula (VII).

This reaction is generally carried out at a temperature of between 100° C. and 170° C.

The reaction mixtures obtained by the various processes described above are treated using conventional physical methods (evaporation, extraction, distillation, crystallization, chromatography and the like) or chemical methods (formation of salts and the like).

The compounds of formula (I), in the form of a free base, may be optionally converted to addition salts with an inorganic or organic acid by the action of such an acid in an organic solvent such as an alcohol, a ketone, an ether or a chlorine-containing solvent.

The compounds of formula (I) and their salts possess advantageous pharmacological properties. These compounds are active against convulsions induced by glutamate and are therefore useful in the treatment and prevention of convulsive phenomena, schizophrenic disorders and especially deficiency forms of schizophrenia, sleep disorders, phenomena linked to cerebral ischaemia as well as neurological conditions where glutamate may be involved, such as Alzheimer's disease, Huntington's disease, lateral amyotrophic sclerosis and olivopontocerebellar atrophy.

The activity of the compounds of formula (I) against convulsions induced by glutamate was determined according to a technique inspired by that of I.P. LAPIN, J. Neural. Transmission, vol. 54, 229–238 , (1982); the injection of glutamate by the intracerebro-venticular route being carried out according to a technique inspired by that of R. CHERMAT and P. SIMON, J. Pharmacol. (Paris), vol. 6, 489–492 (1975). Their $ED_{50}$ is less than or equal to 10 mg/kg.

The compounds of formula (I) have a low toxicity. Their $LD_{50}$ is greater than 15 mg/kg by the I.P. route in mice.

For medicinal use, the compounds of formula (I) may be used as they are or in the form of pharmaceutically acceptable salts, that is to say salts which are nontoxic at the applied doses.

The addition salts with inorganic or organic acids, such as acetate, propionate, succinate, benzoate, fumarate, maleate, oxalate, methanesulphonate, isethionate, theophyllineacetate, salicylate, phenolphthalinate, methylene-bis-$\beta$-oxynaphthoate, hydrochloride, sulphate, nitrate and phosphate may be mentioned as examples of pharmaceutically acceptable salts.

The following examples, which are given with no limitation being implied, show how the invention can be applied in practice.

EXAMPLE 1

A solution of 2.7 g of 2-(N-benzyl-N-methyl)ethanediol in 15 cm³ of dimethylformamide is added to a suspension of 0.75 g of 50% sodium hydride in dispersion in vaseline oil. The reaction medium is stirred for 1 hour at 25° C. 8 g of 2-(2-trifluoroacetylimino-6-trifluoromethoxy-3-benzothiazolinyl)ethyl p-toluenesulphonate are added thereto in small fractions. The mixture is stirred for 12 hours at 25° C. 40 cm³ of ethanol, 8 cm³ of water and 15 cm³ of concentrated ammonium hydroxide (10N) are added to the solution of 2-trifluoroacetylimino-3-{2-[2-(N-methylbenzylamino)ethylthio]ethyl}-6-trifluoromethoxybenzothiazoline thus obtained and the mixture is refluxed for 1 hour. After cooling to 25° C., the mixture is extracted with 2 times 100 cm³ of diethyl ether. The combined organic phases are dried over anhydrous magnesium sulphate and concentrated at 40° C. under reduced pressure (20 mm of mercury; 2.7 kPa). The oil obtained (8 g) is purified by flash chromatography on a silica column, under a nitrogen stream, at medium pressure (0.5–1.5 bar), using an ethyl acetatecyclohexane mixture (90–10 by volume) as eluent. 2.7 g of an oil is isolated which, by the action of oxalic acid in acetone, leads to 3.5 g of 2-imino-3-{2-[2-(N-methylbenzylamino)ethylthio]ethyl}-6-trifluoromethoxybenzothiazoline dioxalate which has a melting point of 205° C.

The 2-(2-trifluoroacetylimino-6-trifluoromethoxy-3-benzothiazolinyl)ethyl p-toluenesulphonate may be prepared according to the following process: 19.3 g of 2-(2-trifluoroacetylimino-6-trifluoromethoxy-3-benzothiazolinyl)ethanol are gradually added to 19.7 g of p-toluenesulphonyl chloride in solution in 120 cm³ of pyridine cooled to 0° C. The reaction is continued for 1 hour at 10°–15° C. The reaction medium is added to 500 cm³ of distilled water and the organic phase is extracted with 3 times 100 cm³ of dichloromethane. After washing with 2 times 50 cm³ of 1N hydrochloric acid and then with 2 times 50 cm³ of distilled water, drying over magnesium sulphate and concentrating to dryness under reduced pressure (20 mm of mercury; 2.7 kPa), 14.1 g of 2-(2-trifluoroacetylimino -6-trifluoromethoxy-3-benzothiazolinyl)ethanol p-toluenesulphonate with a melting point of 143° C. are obtained.

The 2-(2-trifluoroacetylimino-6-trifluoromethoxy-3-benzothiazolinyl)ethanol may be prepared in the following manner: 20.7 g of 2-(2-imino-6-trifluoromethoxy-3-benzothiazolinyl)ethanol hydrobromide, 9.8 g of ethyl trifluoroacetate and 16.1 cm³ of triethylamine are stirred in 100 cm³ of ethanol for 22 hours at a temperature in the region of 20° C. After concentrating to dryness under reduced pressure, the residue obtained is purified by chromatography on a silica column, using ethyl acetate as eluent. 19.2 g of 2-(2-trifluoroacetylimino-6-trifluoromethoxy-3-benzothiazolinyl)ethanol with a melting point of 144° C. are obtained.

The 2-(2-imino-6-trifluoromethoxy-3-benzothiazolinyl)ethanol may be prepared according to the following process: 9.4 g of 2-amino-6-trifluoromethoxybenzothiazole and 10 g of 2-bromoethanol in 30 cm³ of absolute ethanol are heated at boiling temperature for 95 hours. The mixture is then cooled to a temperature in the region of 20° C. The precipitate formed is filtered and washed with 100 cm³ of ethyl ether. 6.4 g of 2-(2-imino-6-trifluoromethoxy-3-benzothiazolinyl)ethanol hydrobromide with a melting point of 219° C. are obtained.

The 2-amino-6-trifluoromethoxybenzothiazole may be prepared according to the method described by L.M. YAGUPOL'SKII et al., Zh. Obshch. Khim. 33(7), 2301 (1963).

EXAMPLE 2

The procedure is carried out as in Example 1, using 1.4 g of 50% sodium hydride dispersed in vaseline oil in 30 cm³ of dimethylformamide and 5.4 g of 1-benzyl-4-mercaptopiperidine in 26 cm³ of dimethylformamide. The mixture is allowed to stand for 1 hour at a temperature in the region of 20° C. 13.7 g of 2-(2-trifluoroacetylimino-6-trifluoromethoxy-3-benzothiazolinyl)ethyl para-toluenesulphonate are added to this suspension over half an hour and the mixture is allowed to stand overnight at a temperature in the region of 20° C., with stirring. 500 cm³ of water are then added and the aqueous solution is extracted with two times 70 cm³ of ethyl acetate, dried over anhydrous magnesium sulphate, filtered and concentrated to dryness at 40° C. under reduced pressure (20 mm of mercury; 2.7 kPa). The oil thus obtained is purified by flash chromatography on a silica column, under a nitrogen stream, at medium pressure (0.5–1.5 bar), using ethyl acetate as eluent. 4.3 g of a beige solid are thus isolated which are introduced into a solution of 172 cm³ of methanol and 51.7 cm³ of a 7% aqueous solution of potassium carbonate. The mixture is allowed to stand for 12 hours at 25° C. and is concentrated to dryness at 70° C. under reduced pressure (20 mm of mercury; 2.7 kPa). 220 cm³ of water and 110 cm³ of ethyl acetate are added. The organic phase is separated, dried over anhydrous magnesium sulphate and concentrated to dryness at 40° C. under reduced pressure (20 mm of mercury; 2.7 kPa). 3.3 g of a yellow oil are thus isolated which is directly taken up in 3 cm³ of 4N hydrochloric ether and 100 cm³ of diethyl ether. 2.4 g of 2-imino-3-{2-[(1-benzyl-4- piperidyl)thio]ethyl}-6-trifluoromethoxybenzothiazoline are thus isolated in dihydrochloride form with a melting point of 200° C.

The 1-benzyl-4-mercaptopiperidine may be prepared in the following manner: 8 g of 1-benzyl-4-acetylthiopiperidine dissolved in 85 cm³ of a 6% aqueous solution of sodium hydroxide are stirred under a nitrogen stream for 16 hours. 10 cm³ of acetic acid and 57.5 g of ammonium sulphate are added to this solution. The mixture is then extracted with two times 100 cm³ of diethyl ether and the organic phase is dried over anhydrous magnesium sulphate and concentrated to dryness at 40° C. under reduced pressure (20 mm of mercury; 2.7 kPa). 5.5 g of 1-benzyl-4-mercaptopiperidine are thus directly isolated in the form of an oil which is used as it is in subsequent synthesis.

The 1-benzyl-4-acetylthiopiperidine may be prepared in the following manner: 16.1 g of diisopropyl azidocarboxylate are added over 10 minutes, with vigorous stirring, at −5° C. and under a nitrogen stream, to 20.8 g of triphenylphosphine dissolved in a mixture of 122 cm³ of tetrahydrofuran and 0.12 cm³ of dimethylformamide. 6.1 g of 1-benzyl-4-hydroxypiperidine are then added at 5° C.

The mixture is heated at 50° C. for 2 hours. The triphenylphosphine oxide thus formed is filtered and the organic solution is washed with 2 times 40 cm³ of water. The organic phase is concentrated to dryness under reduced pressure (20 mm of mercury; 2.7 kPa). 12.35 g of an oil are isolated which is purified by flash chromatography on a silica column, under a nitrogen stream, at medium pressure (0.5–1.5 bar), using a cyclohexane-ethyl acetate mixture (70–30 by volume) as eluent. 8 g of 1-benzyl-4-acetylthiopiperidine are thus obtained in the form of an oil which is used as it is in subsequent synthesis.

EXAMPLE 3

0.86 g of 75% meta-chloroperbenzoic acid is added over 10 minutes to a solution of 1.9 g of 2-imino-3-{2-[(1-benzyl-4-piperidyl)thio]ethyl}-6-trifluoromethoxybenzothioazoline dihydrochloride dissolved in 50 cm³ of a mixture of dioxane and water (50—50 by volume) at a temperature in the region of 20° C. The mixture is stirred at 25° C. for 12 hours and then 100 cm³ of water and 10 cm³ of a 1N aqueous solution of sodium hydroxide are added. The mixture is extracted with two times 100 cm³ of ethyl acetate and then the organic phase is dried over anhydrous magnesium sulphate and concentrated to dryness at 40° C. under reduced pressure (20 mm of mercury; 2.7 kPa). 1.5 g of a colorless oil are obtained which is crystallization from 20 cm³ of diethyl ether. 0.7 g of 2-imino-3-{2-[(1-benzyl-4-piperidyl)sulphinyl]ethyl}-6-trifluoromethoxybenzothiazoline with a melting point of 97° C. is thus obtained.

EXAMPLE 4

0.74 g of 75% m-chloroperbenzoic acid is added over about 15 minutes to 1.42 g of 4-[2-(2-imino-6-trifluoromethoxy-3-benzothiazolinyl)ethylthio]-butyrophenone in solution in 20 cm³ of absolute ethanol cooled to −35° C. The reaction is continued at this temperature for 1 hour. The reaction medium is added to 50 cm³ of ethyl ether and the hydrochloride formed by adding 0.76 cm³ of 4.2N hydrochloric ether. The precipitate is filtered and then recrystallized from methanol. 0.7 g of (RS)-4-[2-(2-imino-6-trifluoromethoxy-3-benzothiazolinyl)ethylsulphinyl]butyrophenone which undergoes sublimation at 170° C. is obtained.

The 4-[2-(2-imino-6-trifluoromethoxy-3-benzothiazolinyl)ethylthio]butyrophenone may be prepared in the following manner: 9.36 g of 2-amino-6-trifluoromethoxybenzothiazole and 10.68 g of 4-(2-chloroethyltio)butyrophenone in 40 cm³ of methyl ethyl ketone are heated at boiling temperature for 72 hours. After cooling to a temperature in the region of 20° C., the reaction medium is concentrated to dryness under reduced pressure. The residue is taken up in distilled water and the organic phase is extracted with dichloromethane after neutralizing with 1N sodium hydroxide. The crude product obtained after the usual treatment is purified by chromatography on a silica column, using an ethyl acetate-cyclohexane mixture (30–70 by volume) as eluent. 3.67 g of 4-[2-(2-imino-6-trifluoromethoxy-3-benzothiazolinyl)ethylthio]butyrophenone with a melting point of 72° C. are obtained after recrystallization from cyclohexane.

The 4-(2-chloroethylthio)butyrophenone may be prepared according to the following process: 11.78 cm³ of thionyl chloride are added dropwise at 0° C. to 29.46 g of 4-(2-hydroxyethylthio)butyrophenone in 80 cm³ of ethyl ether. The reaction medium is heated at boiling temperature for 1 hour. After cooling to a temperature in the region of 20° C. and concentrating to dryness under reduced pressure, the crude product is taken up in 2 times 20 cm³ of ethanol and concentrated to dryness for use in the crude state in the next reaction.

The 4-(2-hydroxyethylthio)butyrophenone may be prepared according to the following process: 18.56 cm³ of 2-mercaptoethanol are added over about 30 minutes to 6.06 g of sodium in 170 cm³ of absolute ethanol, under nitrogen, at a temperature in the region of 20° C., after complete solubilization, followed by 42.25 cm³ of 4-chlorobutyrophenone over about 30 minutes. The reaction medium is heated at boiling temperature for 2 hours. After cooling to a temperature in the region of 20° C., the precipitate formed is filtered and the filtrate is concentrated to dryness under reduced pressure. The crude product is purified by chromatography on a silica column, using an ethyl acetate and cyclohexane mixture (50—50 by volume) as eluent. 29.46 g of 4-(2-hydroxyethylthio)butyrophenone are obtained in the form of a yellow oil which is used as it is in subsequent synthesis.

The 2-amino-6-trifluoromethoxybenzothiazole may be obtained according to the procedure described by L.M. YAGUPOL'SKII et al., Zh. Obshch. Khim., 33(7), 2301 (1963).

EXAMPLE 5

The procedure is carried out as in Example 4, using 2.3 g of 2-imino-3-[2-(3-phenylpropylthio)ethyl]-6-trifluoromethoxybenzothiazoline hydrochloride and 1.18 g of 75% m-chloroperbenzoic acid in 30 cm³ of absolute ethanol. After neutralization with 1N sodium hydroxide, the crude product is purified by chromatography on a silica column, using an ethyl acetate-methanol mixture (90–10 by volume) as eluent. After conversion to the hydrochloride by the addition of 4.2 N hydrochloric ether in ethyl acetate and recrystallization from a mixture of acetone and water (95-5 by volume), 0.65 g of (RS)-2-imino-3-[-2-(3-phenylpropylsulphinyl)ethyl]-6-trifluoromethoxybenzothiazoline hydrochloride with a melting point of 165° C. is obtained.

The 2-imino-3-[2-(3-phenylpropylthio)ethyl]-6-trifluoromethoxybenzothiazoline hydrochloride may be prepared according to the following process: the procedure is carried out as in Example 4 but using 9.5 g of 2-amino-6-trifluoromethoxybenzothiazole and 9.5 g of 1-(2-chloroethylthio)-3-phenylpropane in 40 cm³ of methyl ethyl ketone. 4.7 g of 2-imino-3-[2-(3-phenylpropylthio)ethyl]-6-trifluoromethoxybenzothiazoline hydrochloride with a melting point of 146° C. are obtained after recrystallization from acetonitrile.

The 2-(2-chloroethylthio)-3-phenylpropane may be prepared according to the method described by M. KULKA and F.G. VAN STRYK, Can. J. Chem., 35, 519 (1957).

EXAMPLE 6

3.0 g of N-methyl-N-[2-(4-trifluoromethoxyanilino)ethyl]benzylamine and 3.6 g of potassium thiocyanate in 30 cm³ of acetic acid are treated dropwise with 1.47 g of bromine in solution in 17 cm³ of acetic acid at a temperature in the region of 20° C. The reaction is continued at this temperature for 18 hours. After the addition of 250 cm³ of distilled water, the reaction medium is neutralized with 30% sodium hydroxide and the organic phase is extracted with 2 times 150 cm³ of ethyl acetate, dried over magnesium sulphate and concentrated to dryness under reduced pressure (20 mm of mercury; 2.7 kPa). The residue obtained is purified by chromatography on a silica column, using ethyl acetate as eluent. After formation of the hydrochloride by the addition of 0.9 cm³ of 4.2N hydrochloric ether in 20 cm³ of ethyl acetate, 0.96 g of 3-(N-benzyl-N-methyl-2-aminoethyl)-2-imino-6-trifluoromethoxybenzothiazoline hydrochloride with a melting point of 180° C. is obtained.

The N-methyl-N-[2-(4-trifluoromethoxyanilino)ethyl]benzylamine may be prepared in the following manner: a mixture of 6.0 g of N-p-toluenesulphonyl-2-(4-trifluoromethoxyanilino)ethyl p-toluenesulphonate, 1.51 g of N-methylbenzylamine and 1.05 g of sodium hydrogen carbonate in 100 cm³ of dimethylformamide is heated at 80° C. for 19 hours. After cooling to a temperature in the region of 20° C., the reaction medium is concentrated to dryness under reduced pressure (7 mm of mercury: 0.95 kPa). The residue is washed 2 times with 100 cm³ of distilled water and then taken up in 40 cm³ of absolute ethanol and concentrated to dryness under reduced pressure. The crude product is treated with 26 cm³ of 37% hydrochloric acid in a mixture of acetic acid (26 cm³) and distilled water (17 cm³). The mixture is heated at boiling temperature for 19 hours. After cooling to a temperature in the region of 20° C. and adding to 300 cm³ of distilled water, the aqueous solution is neutralized with 30% sodium hydroxide and the organic phase is extracted with ethyl acetate. 3.34 g of N-methyl-N-[2-(4-trifluoromethoxyanilino)ethyl]benzylamine are obtained in the form of an oil which is used in the crude state in the next reaction.

The N-p-toluenesulphonyl-2-(4-trifluoromethoxyanilino)ethyl p-toluenesulphonate may be prepared according to the following process: 8.6 g of p-toluenesulphonyl chloride are gradually added to 5.0 g of 2-(4-trifluoromethoxyanilino)ethanol and 6.35 cm³ of triethylamine in 50 cm³ of dichloromethane at 0° C. The reaction is continued for 2 hours at a temperature in the region of 20° C. and then the reaction mixture is washed 3 times with 50 cm³ of distilled water.

The organic phase is dried over magnesium sulphate and concentrated to dryness under reduced pressure (20 mm of mercury; 2.7 kPa). After adding 50 cm³ of absolute ethanol, the precipitate formed is filtered. 7.3 g of N-p-toluenesulphonyl-2-(4-trifluoromethoxyanilino)ethyl p-toluenesulphonate with a melting point of 88° C. are obtained.

The 2-(4-trifluoromethoxyanilino)ethanol may be prepared in the following manner: 88.5 g of 4-trifluoromethoxyaniline and 31.2 g of 2-bromoethanol are heated at 160° C. for 1.5 hours. After cooling to a temperature in the region of 20° C., the reaction medium is taken up in 200 cm³ of dichloromethane and the insoluble matter is filtered and the filtrate concentrated to dryness under reduced pressure. After purification by chromatography on a silica column, using an ethyl acetate-cyclohexane mixture (40–60 by volume) as eluent, 26.8 g of 2-(4-trifluoromethoxyanilino)ethanol are obtained in the form of an orange-colored oil.

EXAMPLE 7

By carrying out the procedures as in Example 6, but using 3.92 g of N-(2-phenylethylamine)-N-[2-(4-trifluoromethoxyanilino)ethyl]methylamine, 4.39 g of potassium thiocyanate and 1.65 g of bromine in 60 cm³ of acetic acid, 0.36 g of 2-imino-3-[2-(N-methyl-2-phenylethylamino)ethyl]-6-trifluoromethoxybenzothiazoline dihydrochloride with a melting point of 216° C. is obtained.

The N-(2-phenylethylamine)-N-[2-(4-trifluoromethoxyanilino)ethyl]methylamine may be prepared in the following manner: the procedure is carried out as in Example 6 but using 6 g of N-p-toluenesulphonyl-2-(4-trifluoromethoxyanilino)ethyl p-toluenesulphonate, 1.68 g of N-methyl-2-phenylethylamine and 1.05 g of sodium hydrogen carbonate in 100 cm³ of dimethylformamide. After treating with 26 cm³ of 37% hydrochloric acid, 3.92 g of N-(2-phenylethylamine)-N-[2-(4-trifluoromethoxyanilino)ethyl]methylamine are obtained in the form of an oil which is used in the crude state in the next reaction.

The present invention also relates to the medicinal products consisting of a compound of formula (I) or a salt of such a compound in the pure state or in the form of a composition in which it is combined with any other pharmaceutically compatible product which may be inert or physiologically active. The medicinal products according to the invention may be used orally, parenterally, rectally or topically.

Tablets, pills, powders (gelatine capsules or cachets) or granules may be used as solid compositions for oral administration. In these compositions, the active ingredient according to the invention is mixed with one or more inert diluents such as starch, cellulose, sucrose, lactose or silica.

These compositions may also contain substances other than diluents, for example one or more lubricants such as magnesium stearate or talc, a colorant, a coating (lozenges) or a glaze.

Pharmaceutically acceptable solutions, suspensions, emulsions, syrups and elixirs, containing inert diluents such as water, ethanol, glycerol, vegetable oils or paraffin oil, may be used as liquid compositions for oral administration. These compositions may contain substances other than the diluents, for example wetting, sweetening, thickening, flavoring or stabilizing products.

The sterile compositions for parenteral administration may be preferably solutions which are aqueous or nonaqueous, suspensions or emulsions. Water, propylene glycol, a polyethylene glycol, vegetable oils, in particular olive oil, injectable organic esters, for example ethyl oleate or other suitable organic solvents, may be used as solvent or vehicle. These compositions may also contain adjuvants, in particular wetting, isotonising, emulsifying, dispersing and stabilizing agents. The sterilization may be performed in several ways, for example by asepticizing filtration, by incorporating sterilizing agents into the composition, by irradiation or by heating. They can also be prepared in the form of sterile solid compositions which can be dissolved at the time of use in sterile water or in any other sterile injectable medium.

The compositions for rectal administration are suppositories or rectal capsules which contain, in addition to the active product, excipients such as cocoa butter, semisynthetic glycerides or polyethylene glycols.

The compositions for topical administration may be for example creams, ointments, lotions, collyria, collutories, nasal drops or aerosols.

In human therapy, the compounds according to the invention are particularly useful in the treatment and prevention of convulsive phenomena, schizophrenic disorders and especially deficiency forms of schizophrenia, sleep disorders, phenomena linked to cerebral ischemia as well as neurological conditions where glutamate may be involved, such as Alzheimer's disease, Huntington's disease, lateral amyotrophic sclerosis and olivopontocerebellar atrophy.

The doses depend on the desired effect, the duration of treatment and the mode of administration used; they are generally between 30 and 300 mg per day orally, for an adult, using unit doses ranging from 10 to 100 mg of active substance.

Generally, the doctor will determine the appropriate dosage depending on the age, weight and all other factors specific to the subject to be treated.

The following examples illustrate the compounds according to the invention:

EXAMPLE A

Gelatine capsules containing a dose of 50 mg of active product which have the following composition are prepared according to the usual technique:

| | |
|---|---|
| 2-imino-3-{2-[2-(N-methylbenzyl-amino)ethylthio]ethyl}-6-trifluoromethoxy-benzothiazoline | 50 mg |
| cellulose | 18 mg |
| lactose | 55 mg |
| colloidal silica | 1 mg |
| sodium carboxymethylstarch | 10 mg |
| talc | 10 mg |
| magnesium stearate | 1 mg |

EXAMPLE B

Tablets containing a dose of 50 mg of active product which have the usual composition are prepared according to the usual technique:

| | |
|---|---|
| 2-imino-3-{2-[(1-benzyl-4-piperidyl)sulphinyl]-ethyl}-6-trifluoromethoxybenzothiazoline | 50 mg |
| lactose | 104 mg |
| cellulose | 40 mg |
| polyvidone | 10 mg |
| sodium carboxylmethylstarch | 22 mg |
| talc | 10 mg |
| magnesium stearate | 2 mg |
| colloidal silica | 2 mg |
| mixture of hydroxymethylcellulose, glycerine, titanium oxide (71-3.5-24.5) | qs 1 finished coated tablet containing 245 mg |

EXAMPLE C

An injectable solution containing 10 mg of active product which has the following composition is prepared:

| | |
|---|---|
| 2-imino-3-{2-[2-(N-methylbenzylamino)ethyl-thio]ethyl}-6-trifluoromethoxy-benzothiazoline | 10 mg |
| benzoic acid | 80 mg |
| benzyl alcohol | 0.06 cm³ |
| sodium benzoate | 80 mg |
| 95% ethanol | 0.4 cm³ |
| sodium hydroxide | 24 mg |
| propylene glycol | 1.6 cm³ |
| water | qs 4 cm³ |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

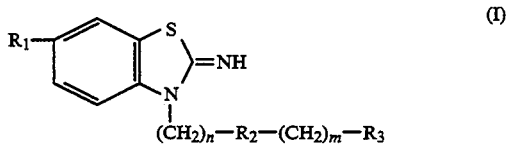

in which $R_1$ represents a polyfluoroalkoxy radical, $R_2$ represents a sulphur or nitrogen atom which is substituted by an alkyl radical or a sulphonyl or sulphinyl radical, $R_3$ represents a phenyl radical, a benzoyl radical, an $NR_4R_5$ radical or a 4-piperidyl radical which is substituted in position 1 by a phenylalkyl radical, $R_4$ represents an alkyl radical, $R_5$ represents a phenylalkyl radical, n is equal to 1, 2 or 3, m is equal to 0, 1, 2 or 3 it being understood that the alkyl radicals and the alkyl and alkoxy moieties contain 1 to 4 carbon atoms in a linear or branched chain, or one of their salts with an inorganic or organic acid.

2. A pharmaceutical composition which comprises as active principle, a pharmaceutically effective amount of compound according to claim 1 or a pharmaceutically acceptable salt of such compound with an inorganic or organic acceptable salt of such compound with an inorganic or organic acid, in association with a compatible pharmaceutically acceptable carrier.

3. A pharmaceutical composition as claimed in claim 2 for the treatment of conditions involving glutamate.

4. A method for the inhibition of glutamate which comprises administering to a subject in need of such treatment an effective amount of a compound of formula (I) as defined in claim 1 or a pharmaceutically acceptable salt of such compound with an inorganic or organic acid.

* * * * *